(12) United States Patent
Tamaoki et al.

(10) Patent No.: US 7,628,958 B2
(45) Date of Patent: Dec. 8, 2009

(54) REACTION DETECTING DEVICE

(75) Inventors: Yuichi Tamaoki, Gunma-ken (JP); Tadahisa Saga, Gunma-ken (JP); Takashi Arai, Gunma-ken (JP); Yasuhiro Kikuchi, Ota (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 362 days.

(21) Appl. No.: 11/497,324

(22) Filed: Aug. 2, 2006

(65) Prior Publication Data

US 2007/0031290 A1 Feb. 8, 2007

(30) Foreign Application Priority Data

Aug. 5, 2005 (JP) .............................. 2005-228314

(51) Int. Cl.
*G01N 21/00* (2006.01)
(52) U.S. Cl. .............. 422/82.05; 422/82.06; 422/82.08; 422/82.09
(58) Field of Classification Search .............. 422/82.05, 422/82.06, 82.07, 82.08, 82.09; 436/164, 436/172
See application file for complete search history.

(56) References Cited

U.S. PATENT DOCUMENTS

| | | | | |
|---|---|---|---|---|
| 5,611,994 A | * | 3/1997 | Bailey et al. ................... | 422/52 |
| 5,643,535 A | * | 7/1997 | Smethers et al. ......... | 422/82.05 |
| 6,057,163 A | * | 5/2000 | McMillan ................... | 436/172 |
| 6,377,342 B1 | * | 4/2002 | Coeurveille ................. | 356/244 |
| 6,818,437 B1 | | 11/2004 | Gambini et al. | |
| 6,852,986 B1 | | 2/2005 | Lee et al. | |
| 2002/0060791 A1 | | 5/2002 | Stumbo et al. | |
| 2003/0215938 A1 | | 11/2003 | Sandell | |

FOREIGN PATENT DOCUMENTS

| | | |
|---|---|---|
| JP | 62-44979 | 11/1987 |
| JP | 10-201464 | 8/1998 |
| JP | 2003-329590 | 11/2003 |
| WO | WO 01/07896 | 2/2001 |
| WO | WO 03/098279 | 11/2003 |
| WO | WO 2004/074820 | 9/2004 |

OTHER PUBLICATIONS

European Search Report dated Dec. 5, 2006 for corresponding EPC Application No. 06117915.6. (7 sheets).

* cited by examiner

*Primary Examiner*—Lyle A Alexander
*Assistant Examiner*—Dwayne K Handy
(74) *Attorney, Agent, or Firm*—Kratz, Quintos & Hanson, LLP

(57) ABSTRACT

An object is to provide a reaction detecting device in which a height dimension of the device itself can be set to be small to realize space saving, unevenness of measurement sensitivity for each reaction container is minimized, and high-sensitivity and high-precision reaction detecting is possible, the device includes: a reflective plate disposed above a temperature controllable reaction block disposed in a reaction chamber constituted in a main body to reflect light; and a light source lamp and a camera arranged in the main body, the light from the light source lamp is reflected by the reflective plate to enter each reaction container from above, and light such as fluorescence directed upwards from a reaction specimen is reflected by the reflective plate to enter the camera.

11 Claims, 10 Drawing Sheets

REACTION DETECTING DEVICE

BACKGROUND OF THE INVENTION

The present invention relates to a reaction detecting device which changes a temperature of a reaction specimen such as deoxyribonucleic acid (DNA) sampled from blood, a test body or the like to promote reaction such as incubation (amplification) and which detects a reaction situation, that is, an amplification amount by incubation.

Heretofore, an incubator is used in amplification of a reaction specimen such as DNA sampled from blood, a test body or the like. This incubator includes an automatic synthesis unit of DNA or RNA by a phosphotriesterification process. The incubator is constituted by covering an outer periphery of a reactor with a thermal block, this thermal block being provided with a thermo module having a heating and cooling function due to the Peltier effect, the thermo module being buried.

In general, a method of synthesizing DNA or the like by the phosphotriesterification process is a method in which four steps of masking, deprotection, drying and condensation are repeated in this order to thereby promote proliferation of DNA. For this purpose, in the synthesis unit, a specimen obtained by mixing DNA and various types of reagents or solutions is placed in the reactor. Electric conduction of the thermo module is controlled by a thermistor to heat the thermal block at +42° C., thereby performing the three steps of masking, drying and condensation. Moreover, a conducting direction of the thermo module is changed to cool the thermal block at +20° C., thereby performing the deprotection step (see Japanese Utility Model Application Laid-Open No. 62-44979).

Moreover, such a DNA synthesis step is executed a plurality of times to thereby amplify DNA up to a predetermined amount. To measure the amplification amount of this reaction specimen, heretofore, at the end of the synthesis, a reaction container is taken out of the incubator, and the amplification amount of DNA, that is, concentration of a reaction liquid is measured using a separately installed reaction detecting device.

The reaction detecting device for use in this case generally measures the amplification amount of a reactant by an optical measurement process. Examples of such a reaction detecting device include devices described in, for example, Japanese Patent Application Laid-Open Nos. 10-201464 and 2003-329590. Here, a basic principle of reaction detecting will be described with reference to a basic conceptual explanatory view of FIG. 12. It is to be noted that a reaction liquid which is a liquid reaction specimen is prepared by a fluorescent dyestuff selected so as to meet excitation requirements of a reaction specimen component which is regarded as a detection object or which is known, and emission or radiation characteristics of the component.

Moreover, this reaction liquid is contained in a reaction container 100 having its top opened. Here, a plurality of reaction containers 100 for use, that is, 96 reaction containers in this case are connected to one another on a plane, and a plurality of reaction specimens can be measured once. The top opening of each reaction container 100 is openably closed by a lid member 101 such as a light transmitting film or cap, and the reaction liquid contained in the container is inhibited from being evaporated. It is to be noted that in FIG. 12, each reaction container 100 is shown in a vertically sectional side view.

It is to be noted that each reaction container 100 containing this reaction liquid is contained in a reaction block 102 formed of a thermally conductive material such as aluminum. In this reaction block 102, there are formed a plurality of holding holes for holding the respective reaction containers 100, 96 holding holes in the present embodiment, so that the respective reaction containers 100 are held. The temperature of this reaction block 102 is controlled to heat or cool the block, thereby incubating (amplifying) the reaction specimen. It is to be noted that the reaction containers 100 contained in the reaction block 102 are pressed in the reaction block 102 by a press member 103 having a good thermal conductivity.

Moreover, a reflective plate 104 constituted of a flat plate is disposed above the reaction containers 100. This reflective plate 104 reflects, toward the reaction containers 100, light from, for example, a light source lamp 105 which emits the light in a direction parallel to the reaction containers 100. In an optical path positioned between this light source lamp 105 and the reflective plate 104, a band pass filter 106 is disposed which transmits only light having a wavelength required for exciting fluorescence among components of the light emitted from the light source lamp 105. Accordingly, from the light emitted from the light source lamp 105, via the band pass filter 106, the only light having the wavelength required for the reaction specimen to excite the fluorescence is obtained via the band pass filter 106, and thereafter the reaction liquid of the reaction container 100 is irradiated.

Thereafter, the reaction liquid in the reaction containers 100 emits the fluorescence in accordance with the concentration of the reaction specimen in the reaction liquid owing to a function of the fluorescent dyestuff. The fluorescence and the reflected light pass through a band pass filter 107 disposed above the reaction containers 100 to irradiate a camera 108 constituting reaction detecting means disposed above the filter. It is to be noted that this band pass filter 107 transmits only the fluorescent component, and the camera 108 is irradiated with the fluorescence only. In FIG. 12, since the reflective plate 104 is constituted of a material which transmits the fluorescence, the fluorescence emitted from the reaction specimen of each reaction container 100 passes through the reflective plate 104 to irradiate the camera 108.

Moreover, when the fluorescence photographed by the camera 108 constituting the reaction detecting means is measured, the reaction specimen can be analyzed, that is, a type or a concentration (amplification amount) of the reaction specimen can be detected.

However, in the reaction detecting device described in the above second document, a plurality of reaction containers contained in the reaction block are provided with the device which optically detects the amplification reaction, but in such a constitution, to once detect the amplification reactions of all the reaction containers, the light from the light source is guided into the reaction containers by use of an optical fiber line. Therefore, there is a problem that costs of components constituting the device increase. Therefore, to avoid the increase of the cost due to the optical fiber line, it is necessary to guide the light from the light source into the reaction specimen in each reaction container at low cost. To receive the fluorescence from the reaction liquid with high sensitivity, it is necessary to guide the light from the light source from above the reaction container, and receive the reflected light including the fluorescence from the light source by the reaction detecting means. This is because in a state in which each reaction container is contained in each holding hole formed in the reaction block, the reaction liquid contained in the reaction container needs to be analyzed.

However, in this case, since it is necessary to dispose the light source and the reaction detecting means above the reaction block, there is a problem that the device enlarges. To solve the problem, it is preferable to shorten an optical path of the fluorescence between the reaction containers and the reaction detecting means, but if the distance is shortened, unevenness is generated in the light emitted from the light source and guided into the reaction liquid of each reaction container via the reflective plate between the reaction container positioned in the center of the reaction block and the reaction container positioned in a peripheral portion. That is, as shown in FIG. 13, unevenness is generated in a received state of the fluorescence detected in the camera 108 between the container in the center and the container in the peripheral portion. This is because the reaction container positioned in the center is irradiated with substantially parallel light, but an incidence angle upon the reaction container positioned in the periphery is not 90°, and this causes a problem that shade is generated by an inner wall of the reaction container, and a part of the incident light from the light source or the fluorescence or the reflected light from the reaction liquid is lacking.

Therefore, as compared with detection sensitivity of the reaction liquid in the reaction container positioned in the center, the detection sensitivity of the reaction liquid in the reaction container positioned in the periphery remarkably drops, and reliability of detection deteriorates. Therefore, there is a problem that in actual, it is not possible to detect the reaction liquid in the reaction container positioned in the periphery.

Therefore, to improve the detection sensitivity of the reaction liquid in the reaction container positioned in the periphery, it is considered that the optical path of the fluorescence between the reaction container and the reaction detecting means be lengthened, but in this case, a height dimension of a main body enlarges as described above. In this case, since the optical path lengthens, there is also a problem that the whole sensitivity deteriorates.

On the other hand, as to the reaction containers contained in the reaction block, an operation to introduce or remove the reaction container needs to be performed every time a measurement object changes. To perform such an operation to introduce or remove the reaction container, a predetermined operation space has to be formed above the reaction block. This requires means for removing the light source or the reaction detecting means from above the reaction block, means for moving the reaction block as such from below the light source or the like.

On the other hand, since the light source or the reaction detecting means is a device requiring a considerable weight, it is difficult to movably constitute the light source or the reaction detecting means. Therefore, it is necessary to move the reaction block as such from below the light source, but this reaction block itself also requires the considerable weight, and therefore special conveyance means is required. Therefore, even in a case where any optical fiber line is not used, since the special conveyance means has to be disposed, there is a problem that the cost soars owing to the increase of the number of expensive components.

Moreover, the reaction detecting device described in the above third document has a constitution in which capillary tubes each containing the reaction liquid are arranged in one row on the plane, a mirror is moved by scanning means to thereby successively guide exciting radiation to each capillary tube in a stepwise manner, and the light is converged on a convergent lens via each capillary tube to thereby send information of a reaction object to a detector. Therefore, the reaction liquid is laterally irradiated with light, and the light transmitted through the reaction liquid is converged by the convergent lens and guided to the detector in the constitution. Therefore, the only capillary tubes that can be arranged in one row on the plane can be detected once, and there is a problem that there is a restriction on the number of the tubes to be detected. Furthermore, there is a problem that all of the light source, the mirror including the scanning means, the reaction block, the respective capillary tubes, the convergent lens and the detecting means have to be constituted on the plane, and an installation area of the device itself enlarges.

SUMMARY OF THE INVENTION

Therefore, the present invention has been developed in order to solve the conventional technical problem, and there is provided a reaction detecting device in which a height dimension of the device itself can be set to be small to realize space saving, unevenness of measurement sensitivity of each reaction container is minimized, and high-sensitivity and high-precision reaction detecting is possible.

In a first aspect of the present invention, there is provided a reaction detecting device which holds a plurality of reaction containers containing reaction specimens or a reaction container having a plurality of dents by a temperature controllable reaction block disposed in a reaction chamber constituted in a main body, the reaction detecting device being configured to detect light from each reaction specimen at a time when each reaction container is irradiated with light, the device comprising: reflection means disposed above the reaction block to reflect the light; and a light source and detection means arranged in the main body, the light from the light source being reflected by the reflection means to enter the reaction container from above, the light directed upwards from the reaction specimen being reflected by the reflection means to enter the detection means.

In a second aspect of the present invention, in the above invention, the reaction detecting device further comprises: light focusing means for converting the light which enters the reaction container from the reflection means into light which is parallel or nearly parallel to the reaction container.

In the reaction detecting device of a third aspect of the present invention, in the above invention, the light focusing means is an optical lens positioned between the reflection means and the reaction container.

In the reaction detecting device of a fourth aspect of the present invention, in the above invention, the optical lens is the Fresnel lens.

In the reaction detecting device of a fifth aspect of the present invention, in the above invention, the Fresnel lens is disposed with a convex surface thereof directed downwards.

In a sixth aspect of the present invention, in the above invention, the reaction detecting device further comprises: a press member which faces an upper portion of the reaction container to heat the reaction container, the optical lens and the press member being integrated at a predetermined interval.

In the reaction detecting device of a seventh aspect of the present invention, in the second aspect of the present invention, the reflection means includes a reflective surface having a predetermined curvature, and functions as the light focusing means.

In an eighth aspect of the present invention, in the above invention, the reaction detecting device further comprises: a cover positioned above the reaction block to openably close the reaction chamber, the cover being configured to interrupt incidence of external light upon the reaction chamber, the reflection means and/or the light focusing means being integrally openably disposed on an inner surface of the cover.

In the reaction detecting device of a ninth aspect of the present invention, in the above invention, the cover moves in an optical path direction between the light source and detection means and the reflection means to openably close the reaction chamber, and the cover is stored in the main body in an opened state.

According to the first aspect of the present invention, the reaction detecting device holds a plurality of reaction containers containing reaction specimens or a reaction container having a plurality of dents by a temperature controllable reaction block disposed in a reaction chamber constituted in a main body, the reaction detecting device being configured to detect the light from each reaction specimen at a time when each reaction container is irradiated with light, the device comprising: the reflection means disposed above the reaction block to reflect the light; and the light source and the detection means arranged in the main body. The light from the light source is reflected by the reflection means to enter the reaction container from above. Moreover, the light directed upwards from the reaction specimen is reflected by the reflection means to enter the detection means. Therefore, the light source and the detection means do not have to be disposed vertically above the reaction block, and a height of the main body can be set to be small. Since the light from the light source is allowed to enter the reaction container from above by the reflection means, it is possible to minimize unevenness of measurement sensitivity for each reaction container without lengthening an optical path. Therefore, the miniaturized device can realize high-sensitivity and high-precision reaction detecting.

According to the second aspect of the present invention, in the above invention, the device includes the light focusing means for converting the light which enters the reaction container from the reflection means into the light which is parallel or nearly parallel to the reaction container. Therefore, it is possible to irradiate the reaction specimen in the reaction container with the light emitted from the light source, reflected by the reflection means, and diffused and decayed radially around an optical axis effectively without wasting the light. Therefore, not only the reaction container positioned in the center but also the reaction container positioned in a peripheral portion can effectively be irradiated with the parallel light or the nearly parallel light, and the unevenness of the measurement sensitivity for each reaction container can be minimized. In consequence, it is possible to realize higher-sensitivity detection.

According to the third aspect of the present invention, in the above invention, since the light focusing means is the optical lens positioned between the reflection means and the reaction container, the reflection means can be constituted of a flat plate. In consequence, it is possible to simplify the constitution of the reflection means, and each reaction container can easily be irradiated with the parallel light or the nearly parallel light.

According to the fourth aspect of the present invention, in the above invention, since the optical lens is the Fresnel lens, the Fresnel lens can allow the light to enter all of the reaction containers substantially right above the reaction containers, and it is possible to effectively correct strain of an image obtained by the irradiation with the light. Moreover, as to any reaction container, the image can enter the detection means without any lack in the same manner as in the reaction container positioned in the center. Therefore, the reaction specimen of each reaction container can be detected with a high measurement sensitivity without any unevenness.

Moreover, since the Fresnel lens is constituted to be comparatively thin as compared with another convex lens, constituting components can be miniaturized, and a constitution in the main body can be simplified.

According to the fifth aspect of the present invention, in the above invention, the Fresnel lens is disposed with the convex surface thereof directed downwards. Since the convex surface of the Fresnel lens having concaves and convexes is directed downwards, it is possible to suppress a disadvantage that dust and the like are deposited on the top of the lens. Moreover, a cleaning property of the surface positioned on the top of the Fresnel lens can be improved, and it is possible to realize stable measurement.

According to the sixth aspect of the present invention, in the above invention, the device further includes: the press member which faces the upper portion of the reaction container to heat the reaction container, and the optical lens and the press member are integrated at the predetermined interval. Therefore, heated air can be held above the reaction container. Therefore, it is possible to prevent generation of fog on the optical lens, and it is possible to improve a detection capability.

In the seventh aspect of the present invention, in the second aspect of the present invention, the reflection means includes the reflective surface having the predetermined curvature, and functions as the light focusing means. Therefore, when the light from the light source, diffused and decayed radially around the optical axis, is reflected by the reflective surface of the reflection means, it is possible to irradiate the reaction specimen in the reaction container effectively without wasting the light. Therefore, not only the reaction container positioned in the center but also the reaction container positioned in the peripheral portion can effectively be irradiated with the parallel light or the nearly parallel light, and the unevenness of the measurement sensitivity for each reaction container can be minimized. In consequence, it is possible to realize higher-sensitivity detection. In such a case, since the reflection means also functions as the light focusing means, it is possible to reduce the number of the components, and the structure can be simplified.

According to the eighth aspect of the present invention, in the above invention, the device further includes the cover positioned above the reaction block to openably close the reaction chamber, the cover being configured to interrupt the incidence of the external light upon the reaction chamber. The reflection means and/or the light focusing means are integrally openably disposed on the inner surface of the cover. Therefore, when the cover is opened, the reflection means can be removed from above the reaction container. In consequence, it is possible to facilitate an operation to introduce or remove the reaction container, and convenience can be improved.

According to the ninth aspect of the present invention, in the above invention, the cover moves in an optical path direction between the light source and detection means and the reflection means to openably close the reaction chamber, and the cover is stored in the main body in the opened state. Therefore, since it is not necessary to install the device in consideration of the opened state of the cover, the device can be constituted to be further compacter. Even when the cover is brought into the opened state, the cove does not obstruct the operation to introduce or remove the reaction container. In

DETAILED DESCRIPTION OF THE PREFERRED EMBODIMENT

Figure 1:
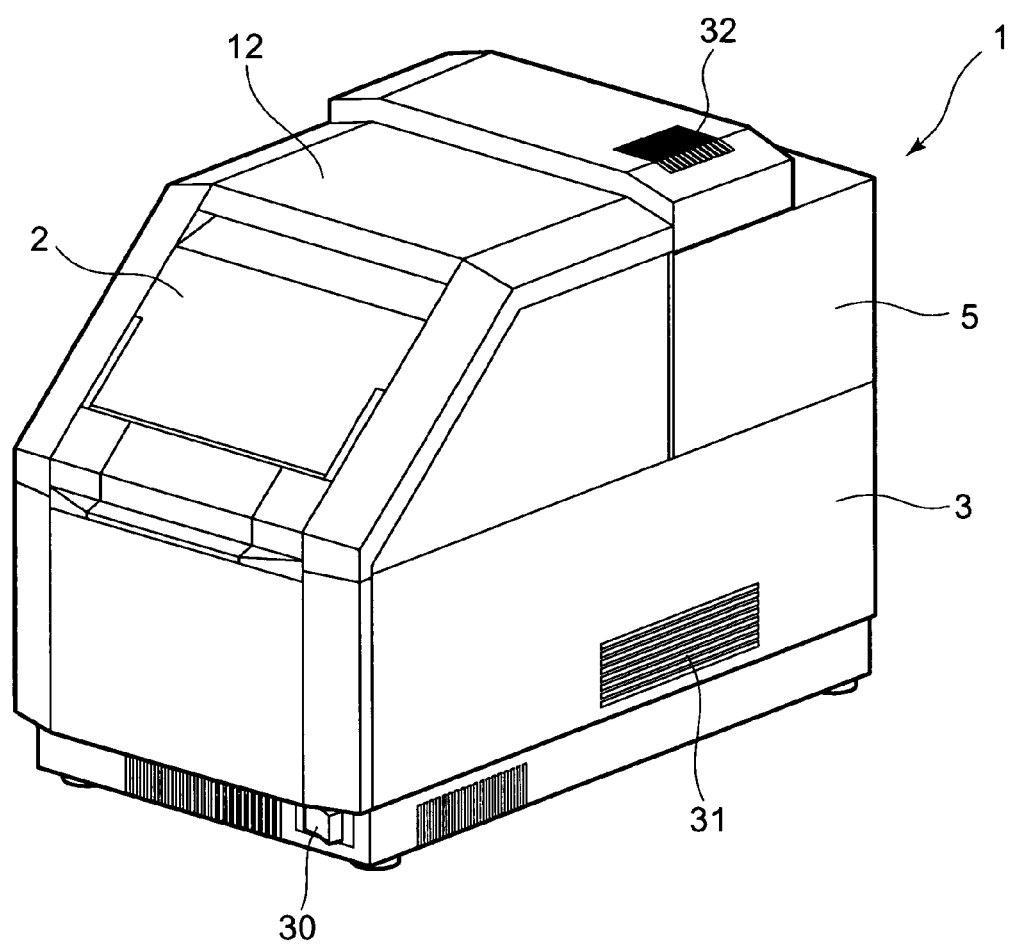
FIG. 1 is a perspective view of a reaction detecting device in an embodiment of the present invention.
Figure 2:
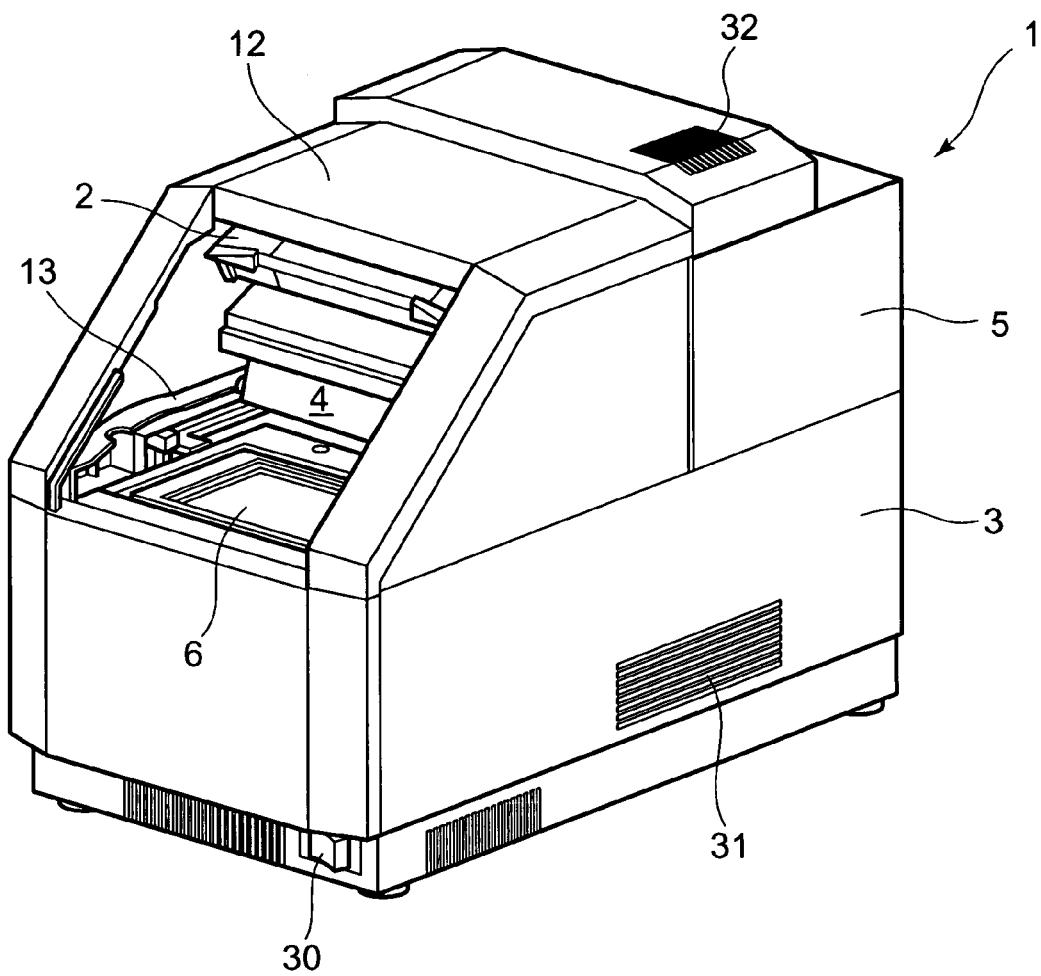
FIG. 2 is a perspective view showing a state in which a cover of the reaction detecting device of FIG. 1 is opened.
Figure 3:
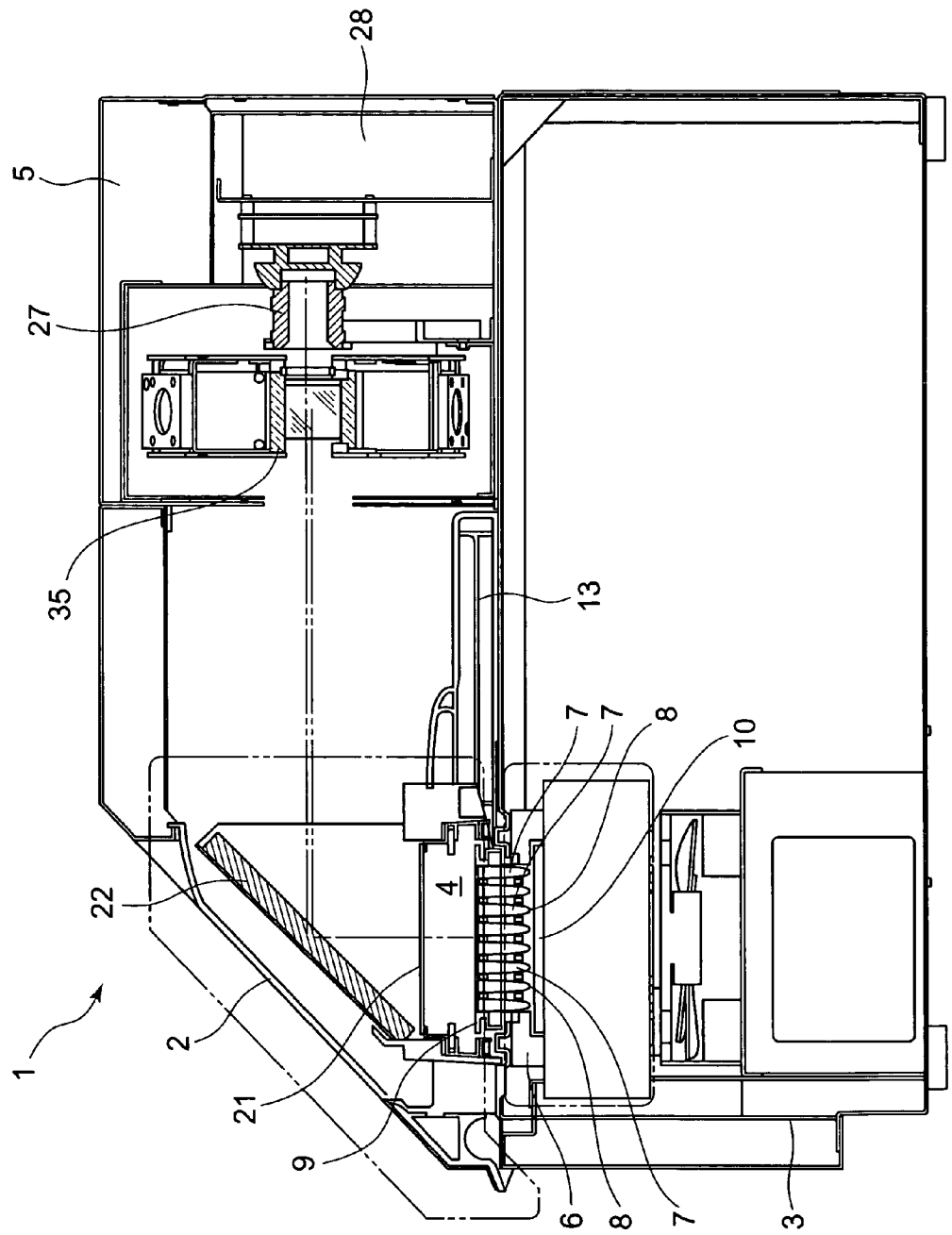
FIG. 3 is a vertically sectional side view showing an inner constitution of the reaction detecting device of FIG. 1.

Embodiments of the present invention will be described hereinafter in detail with reference to the drawings. FIG. 1 is a perspective view of a reaction detecting device 1 in an embodiment of the present invention, FIG. 2 is a perspective view showing a state in which a cover 2 of the reaction detecting device 1 of FIG. 1 is opened, and FIG. 3 is a vertically sectional side view showing an inner constitution of the reaction detecting device 1. The reaction detecting device 1 of the present embodiment is a device which performs proliferation of chromosome DNA as a reaction specimen and which detects a reacted state concerning the proliferation by an optical measurement method.

The reaction detecting device 1 includes: a main body 3 having a reaction chamber 4 formed in the top of the main body; and a reaction detecting section 5 disposed on the top of the main body 3 behind the reaction chamber 4. Moreover, in this reaction chamber 4, there is disposed a reaction block 6 formed of a thermally conductive material such as aluminum. In this reaction block 6, there are formed a plurality of holding holes 8 for holding a plurality of reaction containers 7 containing reaction specimens (reaction liquids) in which DNA, various types of reagents, solutions as culture mediums and the like are mixed. It is to be noted that as the reaction containers 7, other reaction container having a plurality of dents may be used.

Figure 4:
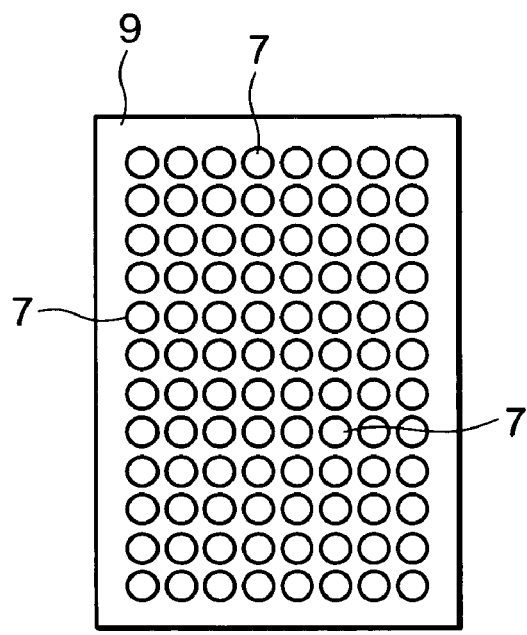
FIG. 4 is a plan view of each reaction container.
Figure 5:
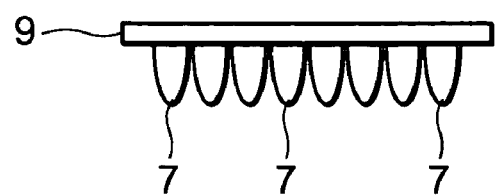
FIG. 5 is a side view of FIG. 4.

As shown in a plan view of FIG. 4 and a side view of FIG. 5, the reaction containers 7 for use in the present embodiment are constituted by integrally forming a plurality of reaction containers 7, in actual, 96 reaction containers 7 in total including 12 longitudinally arranged containers and eight laterally arranged containers. It is to be noted that the number of the reaction containers 7 is not limited to this example. In addition, for example, 384 integrally constituted containers are excellent in handling property. Each reaction container 7 is formed to open in the top, and the top opening is provided with an openable/closable lid member 9 in order to prevent the reaction liquid from being evaporated owing to a thermal treatment. This lid member 9 is constituted to be integrally formed with respect to the top opening of each reaction container 7. In the present embodiment, since the reaction liquid is detected through the lid member 9, a film, a cap or the like constituted of an optically excellent material is used in the member.

Moreover, in this cover 2, the Peltier element 10 is disposed which heats or cools the reaction block 6. It is to be noted that this Peltier element 10 has its temperature controlled by a control unit (not shown) to thereby heat or cool the reaction block 6, whereby the reaction specimen in each reaction container 7 is incubated (amplified).

A dark chamber constituting section 12 is disposed to range from the reaction detecting section 5 disposed in the top of this cover 2 on a rear end to the other end, that is, an upper portion of a front end of the cover 2 having the reaction chamber 4 formed therein in the present embodiment. The front of this dark chamber constituting section 12 is formed to open forwards, and this front opening is openably/closably provided with the cover 2 tilted to descend to the front. Moreover, as shown in FIGS. 2 and 3, this cover 2 is constituted to be movable forwards and backwards by a rail member 13 constituted to range from a front part of the dark chamber constituting section 12, that is, a front portion of the top of the cover 2 to a rear portion in the dark chamber constituting section 12. The cover 2 is stored in the dark chamber constituting section 12 in a state in which the cover is moved rearwards. It is to be noted that in the present embodiment, sides of the dark chamber constituting section 12 are formed to descend toward the front along the tilt of the cover 2 over opposite sides of the cover 2, but this is not restrictive. The cover itself may include opposite sides, and the whole cover constituted of the opposite sides and the front may be stored in the dark chamber constituting section 12.

Figure 6:
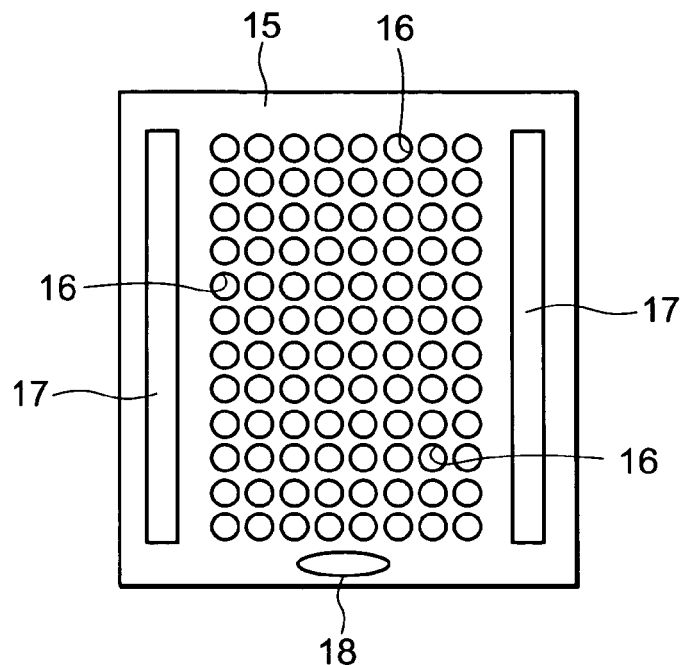
FIG. 6 is a plan view of a press member.
Figure 7:
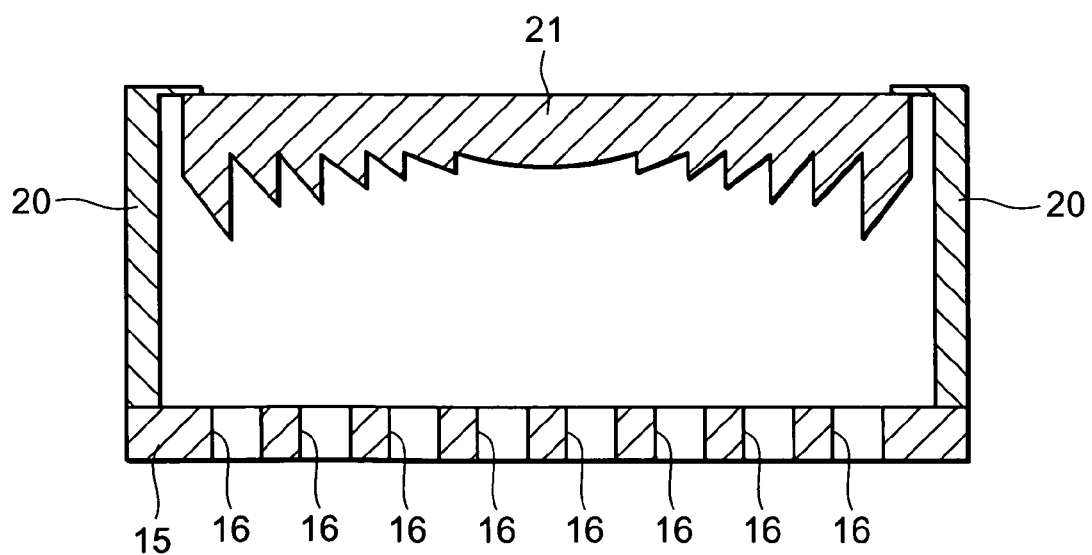
FIG. 7 is a vertically sectional side view of the press member and the Fresnel lens.

Furthermore, in this cover 2, a press member 15 for pressing the reaction container 7 onto the reaction block 6 is integrally movably disposed to face the reaction block 6 of the reaction chamber 4 in a state in which the cover 2 is closed. This press member 15 is plate material constituted of an aluminum material having a good thermal conductivity, and as shown in FIGS. 6 and 7, there are formed a plurality of through holes 16 corresponding to the top openings of the respective reaction containers 7. Moreover, heaters 17, 17 are disposed as upper heating means on, for example, opposite ends of the press member 15. Furthermore, this press member 15 is provided with a temperature sensor 18. Based on an output of the temperature sensor 18, the temperature of each heater 17 is controlled by the control unit. In consequence, there is suppressed a disadvantage of dew condensation on the upper portion of each reaction container 7 or the lid member 9.

In addition, above this press member 15, the Fresnel lens 21 as an optical lens is disposed via connecting members 20. In this Fresnel lens 21, as schematically shown in FIG. 7, a plurality of grooves are generally formed in a plane, and incident light is accordingly refracted and enlarged. At this time, in a case where the incident light is refracted and enlarged, the Fresnel lens 21 has optical characteristics of converging the incident light into a parallel state or a nearly parallel state to transmit the light. Accordingly, the incident light is projected in a state in which strain of each optical path is eliminated.

Moreover, at this time, the Fresnel lens 21 constitutes a space to appropriately hold air between the lens 21 and the press member 15 by the connecting members 20. Therefore, in a state in which the cover 2 is closed, air heated by the heaters 17 disposed in the press member 15 is held above the reaction container 7 to effectively prevent the dew condensation in an upper portion of each reaction container 7. Since the Fresnel lens 21 is not brought into direct contact with each reaction container 7, there is minimized fluctuations of optical characteristics, generated by the fog on the Fresnel lens 21 due to dirt or the like attached to the reaction container 7.

Furthermore, in the present embodiment, as shown in FIG. 7, the Fresnel lens 21 is disposed with a convex surface thereof directed downwards, that is, opposed to the reaction block 6. In consequence, it is possible to suppress a disadvantage that the dust and the like are deposited in the plurality of grooves formed in the Fresnel lens 21, and a cleaning property is improved. Moreover, it is possible to inhibit generation of strain of the light transmitted through the lens. It is to be noted that in the present embodiment, the Fresnel lens 21 is adopted as the optical lens, but the lens may be constituted of another general convex lens. When the Fresnel lens 21 is adopted, however, the optical lens can be constituted to be thin. Therefore, the constitution in the reaction detecting section 5 can be simplified.

On the other hand, above the reaction block 6, a reflective plate 22 is disposed on the surface constituting the reaction chamber 4 side of the cover 2 which is closed above the front of the reaction chamber 4. In the present embodiment, the reflective plate 22 is a mirror or the like constituted of a flat plate, and bends the light from a light source lamp 23 toward the Fresnel lens 21 as described later in detail.

Figure 8:
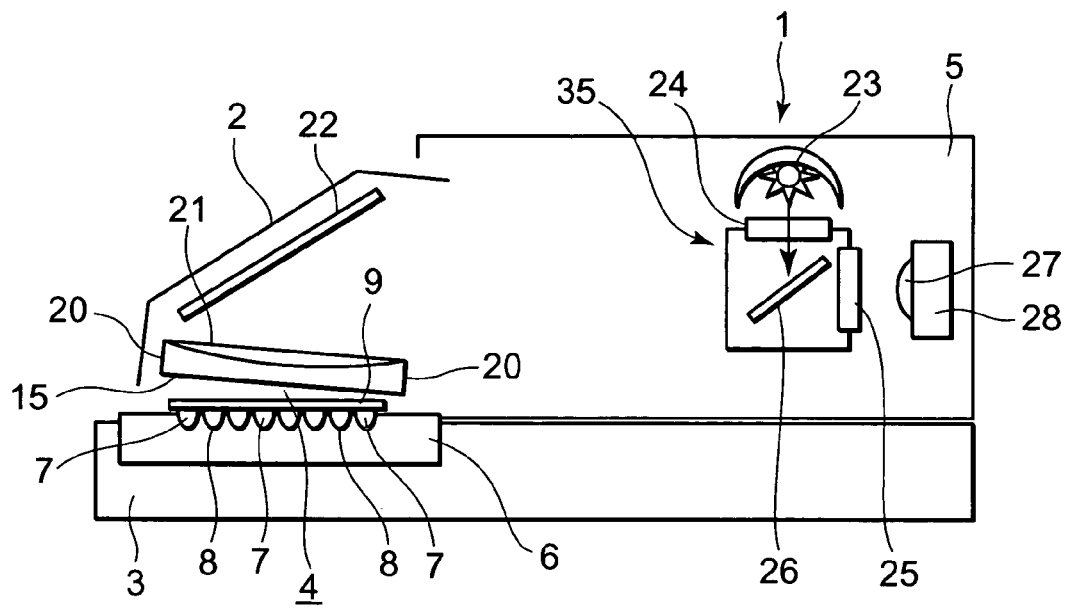
FIG. 8 is a partially enlarged schematic constitution diagram showing the reaction detecting device in a state in which a cover is tilted slightly rearwards.
Figure 9:
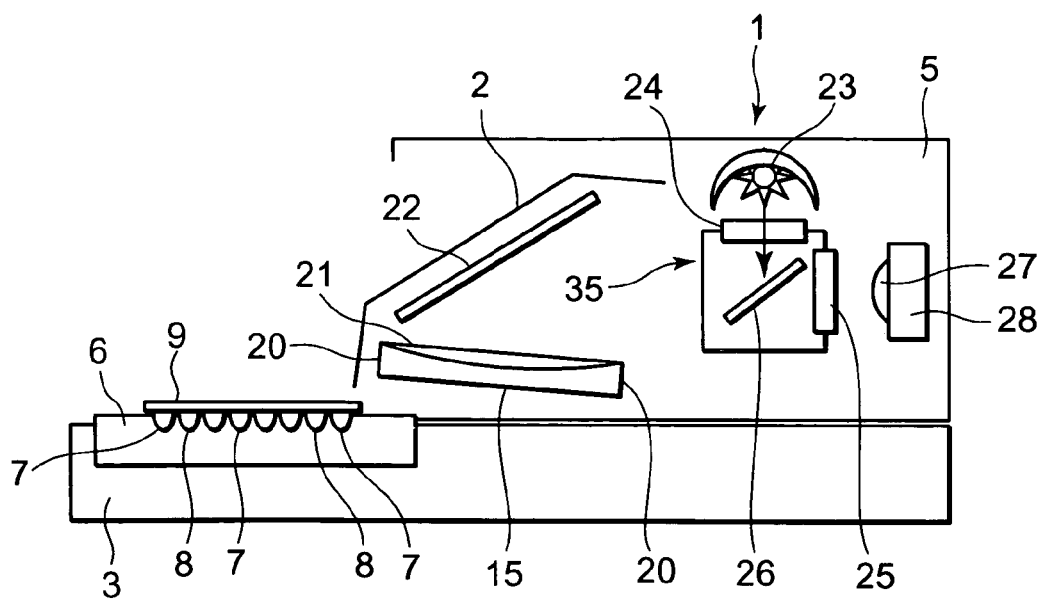
FIG. 9 is a diagram showing a state in which the cover of FIG. 8 is stored in a dark chamber constituting section.

On the other hand, in the reaction detecting section 5, as shown in constitution explanatory views of FIGS. 8 and 9, there are arranged: a filter unit 35 including a plurality of band pass filters; a reflective plate 26; a camera 27 as reaction detecting means; and a reaction analysis section 28 which analyzes a measurement object from an image obtained by the camera 27.

The light source lamp 23 is a lamp which emits light including exciting light to excite fluorescence from the reaction liquid in accordance with an amount of a substance as a detection object in the reaction liquid, and a halogen lamp is generally used. The reflective plate 26 bends the light emitted from the light source lamp 23 at a predetermined angle to polarize the light on the reflective plate 22. This reflective plate 26 has a property of transmitting predetermined fluorescence. In the present embodiment, the light from the light source lamp 23 disposed in an upper portion of the reaction detecting section 5 is bent forwards by the reflective plate 26 to thereby irradiate the reflective plate 22 with the light of the light source lamp 23.

The filter unit 35 is a unit constituted by annularly arranging a plurality of types of band pass filters. The unit is rotated by a driving unit (not shown) to thereby select and position a predetermined band pass filter between the light source lamp 23 and the reflective plate 26 or between the reflective plate 22 and the camera 27. It is to be noted that it is assumed that in the diagram, a band pass filter 24 is positioned between the light source lamp 23 and the reflective plate 26, and a band pass filter 25 is positioned between the reflective plate 22 and the camera 27.

The band pass filter 24 is an optical filter having a property of transmitting light having a wavelength necessary for exciting the fluorescence from the reaction liquid among components of the light from the light source lamp 23, and the light transmitted through the band pass filter 24 is excitation light for exciting the fluorescence from a specific component of the reaction liquid.

The band pass filter 25 is an optical filter having a property of transmitting an only predetermined fluorescence component from the fluorescence and the reflected light emitted from the reaction liquid of the reaction container 7 via the reflective plate 22. Here, the reflected light other than the fluorescence is interrupted.

The camera 27 is a unit which detects the fluorescence transmitted through the band pass filter 25, and based on the fluorescence detected by the camera 27, a concentration, that is, an amplification amount of each reaction liquid is analyzed by the reaction analysis section 28. It is to be noted that as to these band pass filters 24, 25, a combination of these band pass filters 24, 25 is arbitrarily determined and selectively used based on a type of the reaction liquid as the detection object, and further a type of a fluorescence dyestuff for use in accordance with the reaction liquid.

It is to be noted that in FIGS. 1 and 2, a component 30 disposed under the front of the main body 3 is a power supply switch for the reaction detecting device 1. A component 31 disposed on the side of the main body 3 is an exhaust port for discharging an exhaust gas of the main body 3 to the outside, and a component 32 disposed on the top of the reaction detecting section 5 is an exhaust port for discharging exhaust heat of the reaction detecting section 5 to the outside.

According to the above constitution, the control unit controls the Peltier element 10 to perform a thermally denaturing step of setting the reaction liquid in each reaction container 7 held in the holding hole 8 of the reaction block 6 at a thermally denaturing temperature of, for example, +94° C. to thermally denature the reaction liquid. Subsequently, the control unit controls the Peltier cooling element 10 to perform an annealing step and an extending step of cooling the reaction block 6 at, for example, +37° C.; to anneal and extend the reaction specimen in the reaction liquid contained in each reaction container 7 and thermally denatured. The control unit repeats one cycle including this thermally denaturing step, the annealing step and the extending step a plurality of times such as 30 times to thereby incubate (amplify) DNA or the like by a PCR process.

In the process of this incubation or at the end of the incubation, the reaction detecting section 5 executes a detecting operation arbitrarily or periodically, for example, after the end of one cycle in order to detect an amplified state of the reaction liquid in each reaction container 7. In the detecting operation, first the light emitted from the light source lamp 23 reaches the reflective plate 26 via the band pass filter 24. The band pass filter 24 transmits the light having the wavelength necessary for exciting the fluorescence in the light from the light source lamp 23, that is, the only excitation light. The reflective plate 26 allows the excitation light to pass through the dark chamber constituting section 12 toward the reflective plate 22. Furthermore, the reflective plate 22 directs the excitation light toward the Fresnel lens 21 opposed to the reaction block 6. That is, the light is transmitted downwards from above.

The excitation light with which the Fresnel lens 21 has been irradiated is focused by the optical characteristics of the lens 21, and an incidence angle of the light is changed to such an angle that is parallel or nearly parallel to each reaction container 7 contained in the reaction block 6. Accordingly, the excitation light transmitted through the lens 21 is allowed to enter each reaction container 7 at such an incidence angle that is parallel or nearly parallel to the container via each through hole 16 formed in the press member 15.

The reaction specimen in each reaction container 7 to which a predetermined fluorescent dyestuff has been added beforehand is irradiated with the excitation light which has entered the reaction container 7 at such an angle that is parallel or nearly parallel to the container, and accordingly the fluorescent is emitted in accordance with an amount of the reaction specimen. This generated fluorescence and the reflected light from another reaction specimen similarly reach the reflective plate 22 via each through hole 16 formed in the press member 15 and the Fresnel lens 21.

Thereafter, the fluorescence and the other reflected light which have reached the reflective plate 22 reaches the camera 27 via the band pass filter 25 disposed to face the reflective plate 22, while forming the optical path in a substantially horizontal direction in the dark chamber constituting section 12 owing to the function of the reflective plate 22. In this case, since the cover 2 is closed to thereby constitute a dark chamber in the dark chamber constituting section 12, it is possible to suppress a disadvantage that the fluorescence is decayed.

A this time, since the reflective plate 26 is constituted of a material capable of transmitting the fluorescence, the band pass filter 25 is irradiated with the reflected light and the fluorescence transmitted through the reflective plate 26. Since the band pass filter 25 can transmit the only predetermined fluorescence in accordance with the type of the band pass filter 25 as described, the camera 27 disposed behind the filter is irradiated with the only predetermined fluorescence.

Moreover, when the camera 27 photographs the received fluorescence, it is possible to detect a fluorescent state of the reaction specimen in each reaction container 7. Moreover, when the detected fluorescent state of each reaction specimen is analyzed in the reaction analysis section 28, it is possible to detect the concentration of each specimen, that is, the amplification amount of DNA or the like. It is to be noted that since a technique to detect and analyze the amplification amount of DNA or the like from the fluorescence is similar to a known technology, description thereof is omitted.

Furthermore, in the present embodiment, in a case where an operation to introduce or remove each reaction container 7 is performed, as shown in FIGS. 8 and 9, first, after tilting the front end of the cover 2 slightly rearwards, the cover is slid rearwards along the rail member 13, that is, in a direction of an optical path between the light source lamp 23 and camera 27 and the reflective plate 22. Accordingly, the cover 2 is stored in the dark chamber constituting section 12 in an opened state, and opened above the reaction block 6. Therefore, since the cover 2 does not obstruct the operation to introduce or remove each reaction container 7, the operation to introduce or remove the reaction container 7 can easily be performed. It is to be noted that in this case, the press member 15 for pressing the reaction container 7 onto the reaction block 6, the Fresnel lens 21 and the like are retracted rearwards together with the cover 2, and stored in the dark chamber constituting section 12. Therefore, it is possible to easily open each reaction container 7 from above by one operation to open the cover 2, and convenience is enhanced.

Moreover, according to such a constitution of the cover 2, the device does not have to be installed in consideration of the opened state of the cover 2, and the device can be constituted to be further compacter. Therefore, in a case where a plurality of reaction detecting devices 1 are arranged in a rack or the like, it is not necessary to arrange the devices in consideration of the opened state of the cover 2, and space saving can be realized.

As described above, the reaction detecting device 1 of the present invention holds a plurality of reaction containers 7 containing the reaction specimens by the temperature controllable reaction block 6 disposed in the reaction chamber 4 constituted in the main body 3. Moreover, the device detects the light from the reaction specimen at a time when the reaction container 7 is irradiated with light. The device includes: the reaction detecting section 5 disposed in one end of the main body 3, which is the rear end of the top of the main body 3 in the present embodiment, to detect the light from the reaction specimen; the cover 2 positioned above the reaction block 6 in the other end of the top of the main body 3, which is the front end in the present embodiment; and the dark chamber constituting section 12 constituting the dark chamber between the cover 2 and the reaction detecting section 5. The cover 2 has the inclined surface formed to descend externally from the inside. Moreover, the cover includes: the reflective plate 22 disposed on the inclined surface positioned on the side of the reaction block 6; and the Fresnel lens 21 as the optical lens positioned above each reaction container 7 contained in the reaction block 6. Moreover, the reaction detecting section 5 includes the light source lamp 23, the band pass filters 24, 25, the camera 27 as the detection means and the reaction analysis section 28. Furthermore, the light directed upwards from the light source lamp 23 is reflected by the 22 to enter each reaction container 7 from above, and the light directed upwards from the reaction specimen of the reaction container 7 is reflected by the reflective plate 22 to enter the reaction detecting section 5.

Therefore, the reaction detecting section 5 including the light source lamp 23, the band pass filters 24, 25, the reflective plate 26, the camera 27, the reaction analysis section 28 and the like does not have to be disposed perpendicularly above the reaction block 6. Therefore, the height dimension of the reaction detecting device 1 can be set to be small. Since the reflective plate 22 allows the light from the light source lamp 23 to enter each reaction container 7 from above, the unevenness of the measurement sensitivity for each reaction container 7 can be minimized. Therefore, the miniaturized device can realize high-sensitivity and high-precision reaction detecting.

Especially in the present embodiment, as the light focusing means, the Fresnel lens (optical lens) 21 is disposed which converts the light entering each reaction container 7 from the reflective plate 22 into the light parallel or nearly parallel to the reaction container 7. Therefore, it is possible to irradiate the reaction specimen in the reaction container 7 with the light from the light source lamp 23, reflected by the reflective plate 22, and diffused and decayed radially around the optical axis effectively without wasting the light.

Figure 10:
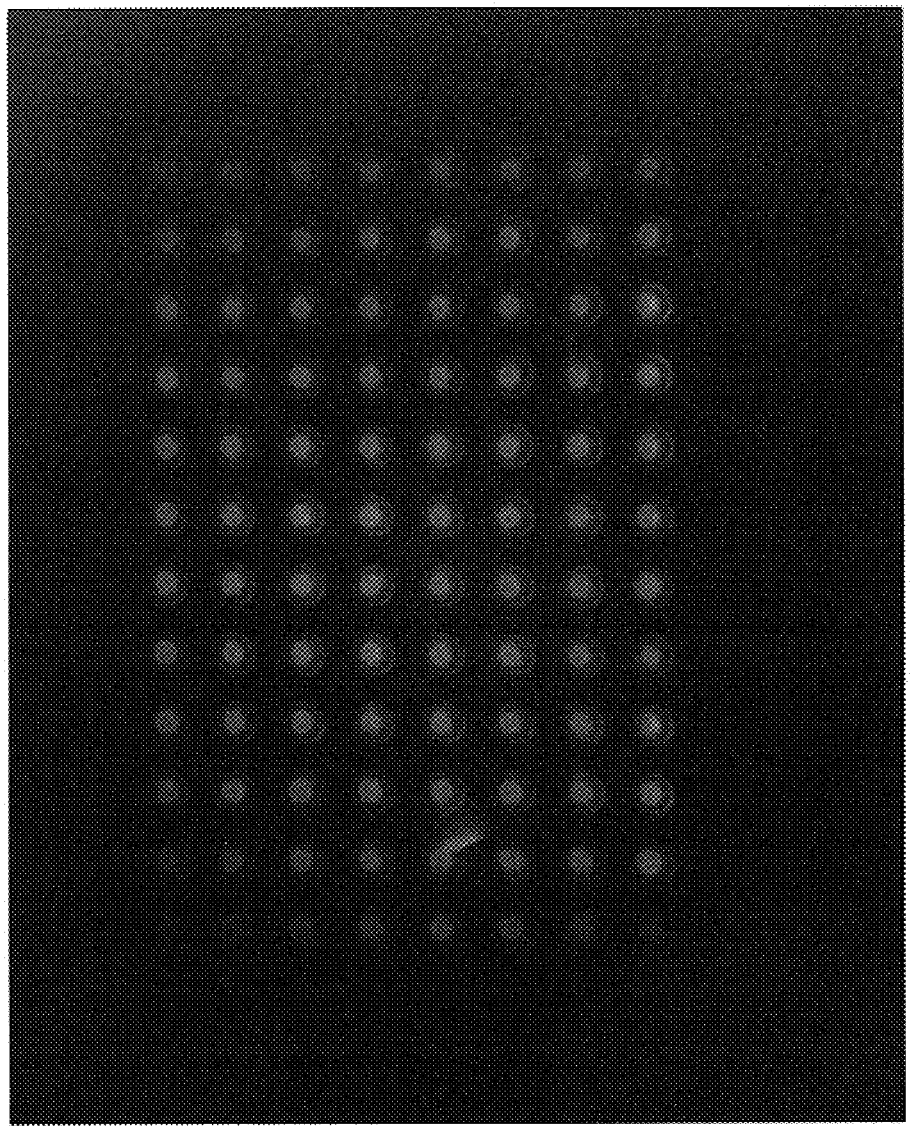
FIG. 10 is a diagram showing a detected image obtained by the present embodiment.

Therefore, since not only the reaction container 7 disposed in the center but also the reaction container 7 disposed in the peripheral portion can effectively be irradiated with the parallel light or the nearly parallel light, as shown in FIG. 10 showing the image actually detected by the camera 27 in the present embodiment, the unevenness of the measurement sensitivity for each reaction container 7 can be minimized. In consequence, it is possible to realize high-sensitivity detection without being influenced by the position where the reaction container 7 is disposed.

Especially in the present embodiment, since the Fresnel lens 21 as the optical lens is disposed between the reflective plate 22 and the reaction container 7, the reflective plate 22 can be constituted of the flat plate. Therefore, while simplifying the constitution of the reflective plate 22, it is possible to easily irradiate each reaction container 7 with the parallel or nearly parallel light.

Moreover, the Fresnel lens 21 for use in the present invention allows the light to enter all of the reaction containers 7 substantially right from above, and the strain of the image obtained by the irradiation with the light can effectively be corrected. Therefore, even as to any reaction container 7, the image can enter the detection means without any lack in the same manner as in the reaction container 7 positioned in the center. Therefore, the reaction specimen of each reaction container 7 can be detected with the high measurement sensitivity without any unevenness.

Furthermore, as described in detail, since the press member 15 to heat the reaction container 7 is constituted by integrating the Fresnel lens 21 and the press member 15 at the predetermined interval, the Fresnel lens 21 and the press member 15 can hold heated air in the upper portion of the reaction container 7. In consequence, the generation of the fog on the Fresnel lens 21 can be eliminated. Since the influence of the fog is avoided, the detection capability can be improved.

Figure 11:
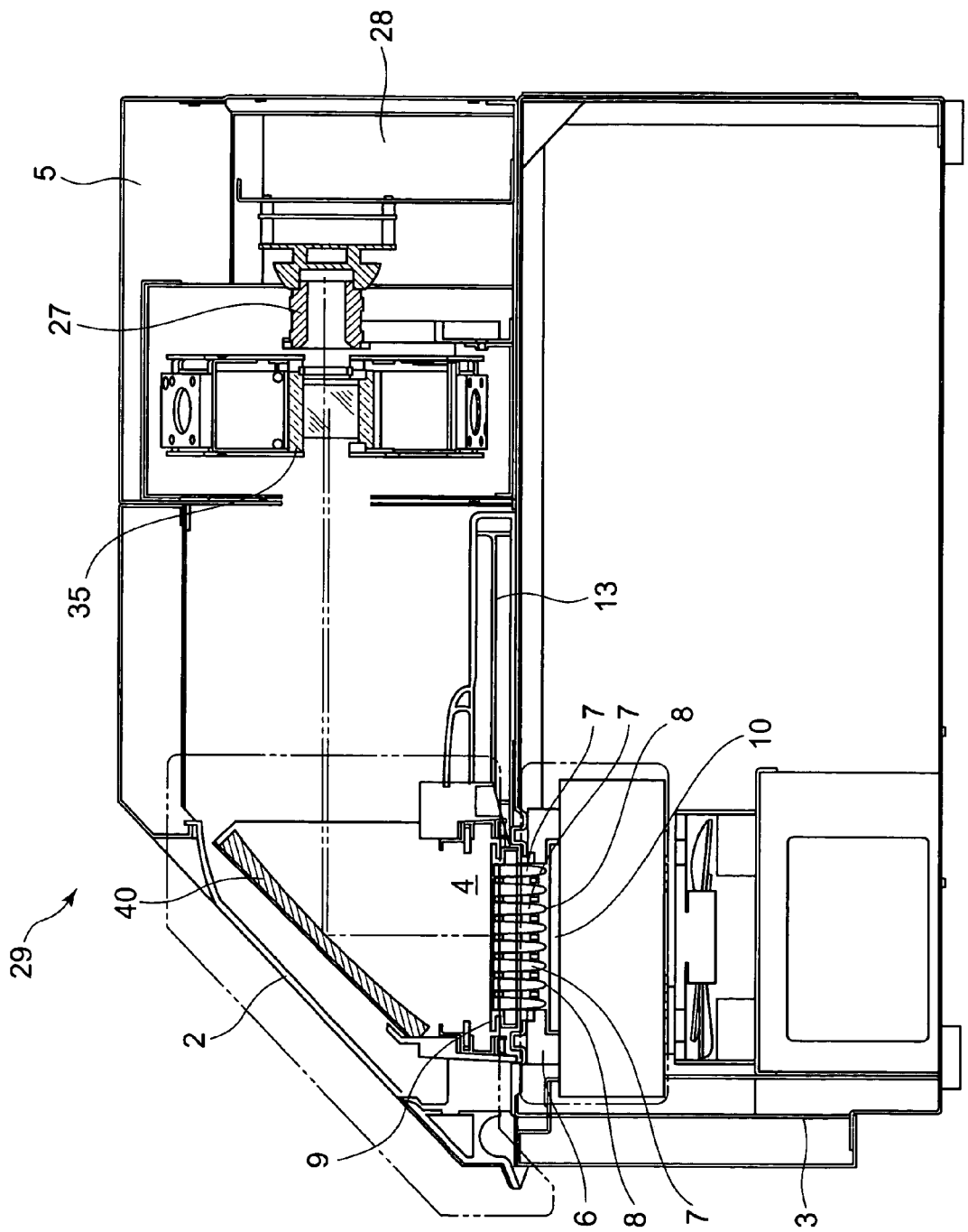
FIG. 11 is a vertically sectional side view showing an inner constitution of a reaction detecting device in another embodiment.
Figure 12:
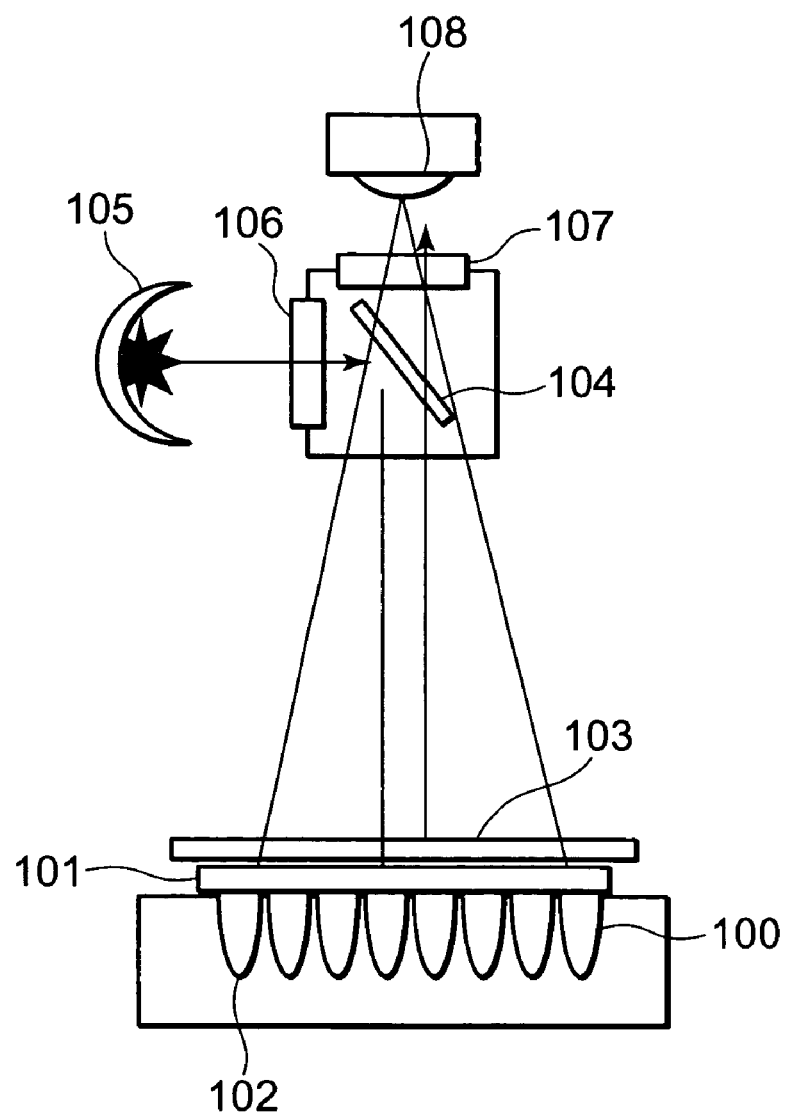
FIG. 12 is a basic concept explanatory view of an optical measurement process.
Figure 13:
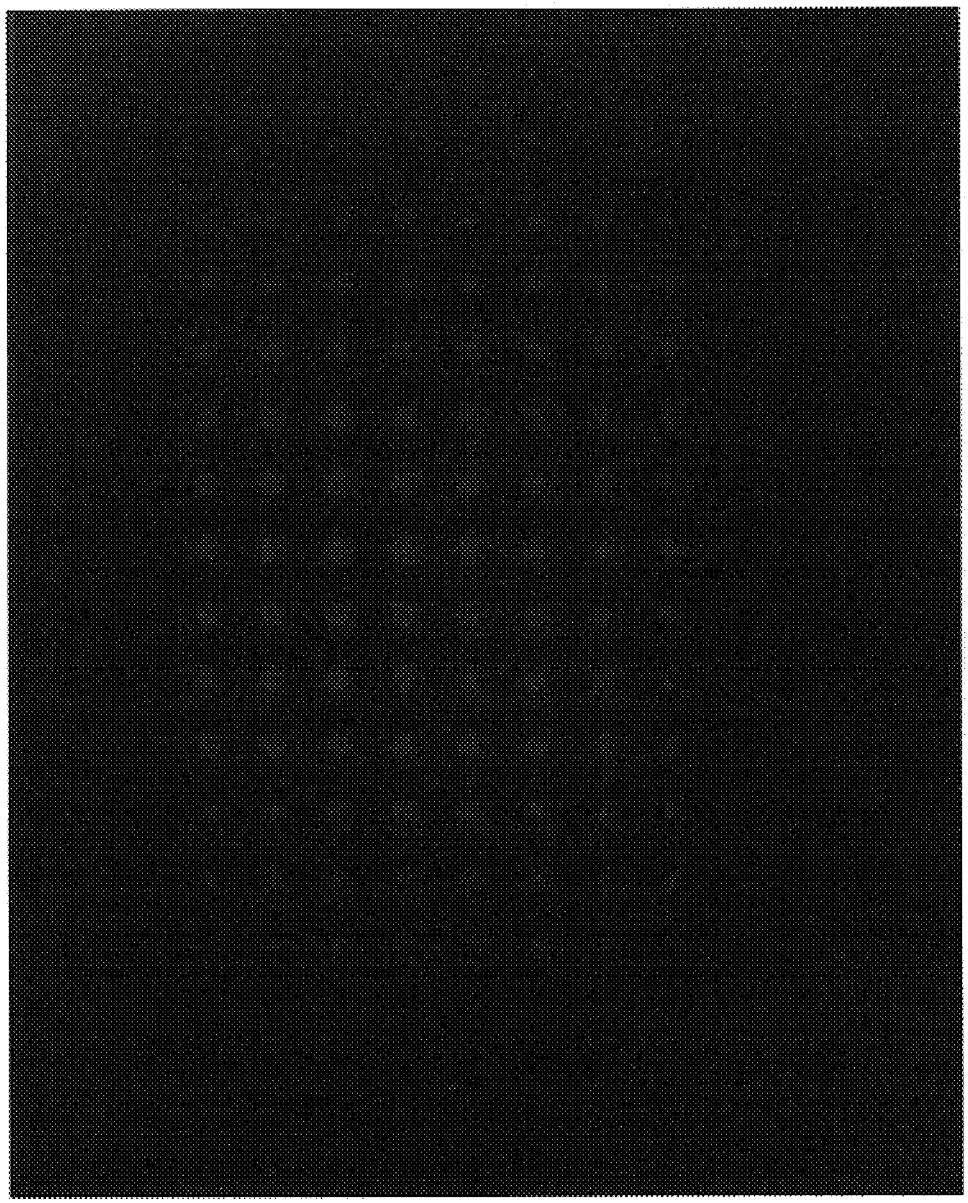
FIG. 13 is a diagram showing a detected image obtained by conventional optical measurement.

It is to be noted that in the above embodiment, as the light focusing means, an optical lens such as the Fresnel lens 21 is used, but the means is not limited to this lens. That is, as in a reaction detecting device 29 in another embodiment shown in FIG. 11, light focusing means may be constituted of a reflective plate 40 including a reflective surface disposed on a surface constituting the cover 2 on the side of a reaction chamber 4 and having a predetermined curvature, such as a reflective plate having an aspherical surface.

The reflective plate 40 includes the reflective surface formed at such a curvature that the reaction specimen in each reaction container 7 can be irradiated with the light from the light source lamp 23, diffused and decayed radially around the optical axis, effectively without wasting the light. Therefore, in the same manner as in the embodiment, not only the reaction container 7 disposed in the center but also the reaction container 7 disposed in the peripheral portion can effectively be irradiated with the parallel or nearly parallel light, and the unevenness of the measurement sensitivity for each reaction container 7 can be minimized. In consequence, the higher-sensitivity detection can be realized. In such a case, since the reflective plate 40 has a reflecting function, and also functions as the light focusing means, the number of the components can be reduced, and the structure can be simplified.

What is claimed is:

1. A reaction detecting device to hold a plurality of reaction containers to contain reaction specimens or a reaction container having a plurality of dents in a temperature controllable reaction block; the reaction detecting device comprising:
    a reaction chamber constituted in a dark chamber in a main body of the reaction detecting device;
    a light source lamp inside the dark chamber;
    a detector, inside the dark chamber, being configured to detect light from each reaction specimen at a time when each reaction specimen is irradiated with light from the light source lamp;
    a reflector disposed above the reaction block configured to reflect the light from the light source lamp onto the reaction block in the reaction chamber from above, and light directed outwards from the reaction specimen being reflected by the reflector to enter the detector; and
    a cover configured to interrupt incidence of external light upon the reaction chamber in a closed state, wherein the cover moves in an optical path direction between the light source the detector and the reflector to openably close the dark chamber, and the cover is stored in the main body in an opened state.

2. The reaction detecting device according to claim 1, further comprising:
    light focusing means to convert the light which enters the reaction container from the reflector into light which is parallel or nearly parallel to the reaction container.

3. The reaction detecting device according to claim 2, wherein the light focusing means comprises an optical lens positioned between the reflector and the reaction container.

4. The reaction detecting device according to claim 3, wherein the optical lens is a Fresnel lens.

5. The reaction detecting device according to claim 4, wherein the Fresnel lens is disposed with a convex surface thereof directed downwards.

6. The reaction detecting device according to claim 5, further comprising:
    a press member which faces an upper portion of the reaction container to heat the reaction container, the optical lens and the press member being integrated at a predetermined interval.

7. The reaction detecting device according to claim 2, wherein the reflector includes a reflective surface having a predetermined curvature, and functions as the light focusing means.

8. The reaction detecting device according to claim 1, wherein the cover is positioned above the reaction block to openably close the reaction chamber,
    and wherein the reflector and/or the light focusing means is mounted on an inner surface of the cover.

9. The reaction detecting device according to claim 1, comprising a rail on which the cover is rearwardly slidable in the optical path direction.

10. The reaction detecting device according to claim 9, wherein the cover is rearwardly slidable in the optical path direction after tilting a front end of the cover slightly rearwards.

11. The reaction detecting device according to claim 9, comprising
    an optical lens positioned between the reflector and the reaction container as a light focusing means, and
    a press member which faces an upper portion of the reaction container to heat the reaction container, the optical lens and the press member being integrated at a predetermined interval,
    wherein the press member and the lens are retracted retractable rearwards together with the cover.

* * * * *